United States Patent [19]

Bates

[11] Patent Number: 4,966,136

[45] Date of Patent: Oct. 30, 1990

[54] ORTHOPEDIC SUPPORT DEVICE

[76] Inventor: Norman R. Bates, 89 Niagara Street, Toronto, Ontario, Canada

[21] Appl. No.: 334,188

[22] Filed: Apr. 6, 1989

[30] Foreign Application Priority Data

Sep. 2, 1988 [CA] Canada .................................. 576495

[51] Int. Cl.⁵ .............................................. A61H 1/02
[52] U.S. Cl. ......................... 128/87 R; 128/DIG. 15; 128/DIG. 19; 128/DIG. 23
[58] Field of Search .................. 128/87 R, 87 B, 155, 128/156, DIG. 15, DIG. 19, DIG. 23, 82

[56] References Cited

U.S. PATENT DOCUMENTS

| | | | |
|---|---|---|---|
| 3,075,521 | 1/1963 | Grassl | 128/87 R X |
| 3,338,236 | 8/1967 | McLeod, Jr. | 128/DIG. 19 X |
| 3,374,785 | 3/1968 | Gaylord, Jr. | 128/87 R X |
| 3,504,667 | 4/1970 | McFarlane | 128/87 R X |
| 3,696,810 | 10/1972 | Gaylord, Jr. | 128/DIG. 15 X |
| 3,718,137 | 2/1973 | Gaylord, Jr. | 128/DIG. 19 X |
| 3,857,388 | 12/1974 | Frankel | 128/87 R |
| 3,897,776 | 8/1975 | Gaylord, Jr. | 128/DIG. 19 X |
| 4,232,663 | 11/1980 | Newton | 128/DIG. 23 X |
| 4,313,437 | 2/1982 | Martin | 128/DIG. 15 |
| 4,819,622 | 4/1989 | Taylor et al. | 128/DIG. 23 X |

FOREIGN PATENT DOCUMENTS 734222  5/1966  Canada .................... 128/DIG. 23

Primary Examiner—Randolph A. Reese
Assistant Examiner—Jeffrey L. Thompson
Attorney, Agent, or Firm—Leighton K. Chong

[57] ABSTRACT

An orthopedic support device comprises a resilient pad having a length and a width, covered by a woven or non-woven fabric having a pair of ends which are adapted to be joined together, whereby the support device may be wrapped around a body at a desired location, and the ends of the device fastened together to support the body at that location, characterized in that the device is provided with a lengthwise extending first strip of hook and pile closure material, and there provided, in association with the device, a complementary second strip of hook and pile closure material, whereby the ends of the device may be releasably fastened together with a complementary strip of closure material.

6 Claims, 2 Drawing Sheets

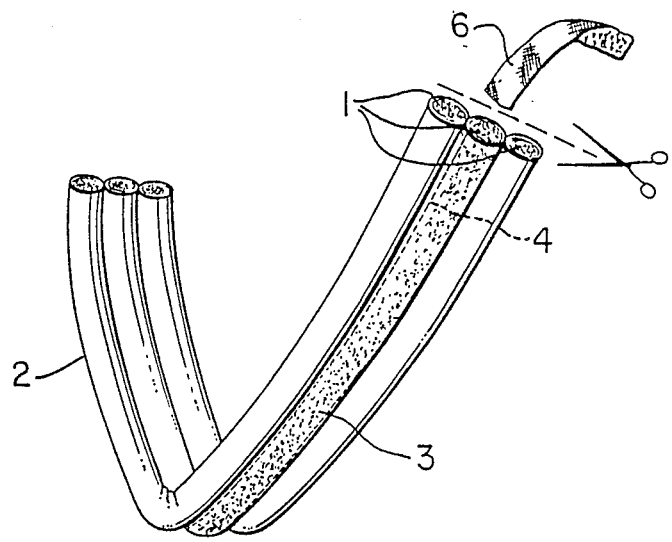
FIG. 1
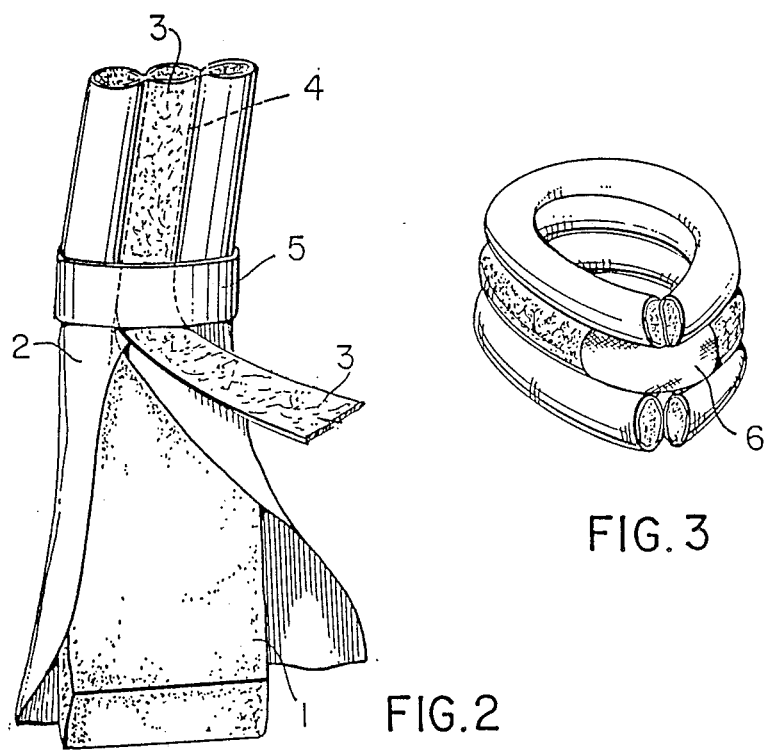
FIG. 2
FIG. 3

ORTHOPEDIC SUPPORT DEVICE

The present invention relates to the field of orthopedic devices and supports. Specifically, the present invention relates to a new orthopedic support collar, and a method of manufacturing same.

Orthopedic support collars, or as they are also known, cervical collars, are generally indicated for cases of neck sprain or strain. They exist in several different forms, and in the case of known collars most relevant to the present invention, comprise lengths of foam padding covered with textile material. One end of the foam padding is provided with a hook and pile closure strip (such as a Velcro TM strip) and the other end is provided with a complementary strip of hook and pile closure material so that when the two ends are brought together they can be fastened one to another.

Generally speaking, this type of collar is very effective in immobilizing injured necks and is in current use with, for instance, Fire Departments in North America. The principle draw back of this type of cervical collar is that for hospital emergency room, or a crew of emergency medics or firefighters to be properly equipped, they must have with them cervical collars capable of fitting several different sizes of necks. This increases the amount of equipment which must be carried by any one unit, and also increases the likelihood that the wrong size of collar will be used on a given victim.

Another, more simple form of soft cervical collar, commonly known as a rough collar, can be made by inserting a piece of supportive material such as a roll of padding or a piece of foam into a tubular piece of elastic stockinette. The rough collar is held around the neck of the victim by tying the loose ends of the stockinette together. Commonly, several tubes of stockinette are worn stacked on top of each other in order to provide a support of adequate height.

Another form of cervical collar may be made from a rectangular piece of felt, which may or may not be cut down at the top middle section, or contour cut. This piece of felt is inserted into a piece of elastic stockinette which is tied together at the back of the victim's neck.

The object of the present invention is to provide a cervical collar for use in a clinical setting or in the field, which may be adapted to fit persons with various neck sizes, and which thereby obviate the need for carrying more than one length of collar.

Other objects of the present invention will become obvious upon reading the description and claims.

In a first broad aspect, the present invention relates to an orthopedic support device comprising a resilient pad having a length and a width, covered by a woven or non-woven fabric having a pair of ends which are adapted to be joined together, whereby said support device may be wrapped around a body at a desired location, and the ends of said device fastened together to support the body at that location, characterized in that: said device is provided with a lengthwise extending first strip of hook and pile closure material, and there provided, in association with said device, a complementary second strip of hook and pile closure material, whereby the ends of said device may be releasably fastened together with said complementary strip of closure material.

In a second broad aspect, the present invention relates to a method of manufacturing an orthopedic support device, comprising the steps of: providing a length of resilient foam padding; covering said foam padding with a fabric material on a continuous basis; stitching a strip of hook and pile closure material to said foam, over said fabric material; and providing one or more complementary strips of hook and pile closure, whereby a said length of foam may be cut at any desired location to provide a support device of a desired length, and said complementary strip of closure will fasten the ends thereof together.

In drawings which illustrate the present invention by way of example:

FIG. 1 is a perspective view of a length of orthopedic support material according to the present invention;

FIG. 2 is a perspective view of a length of orthopedic support material according to the present invention at a point during the manufacturing process thereof;

FIG. 3 is a perspective view of a cervical collar according to the present invention;

Figure 4:
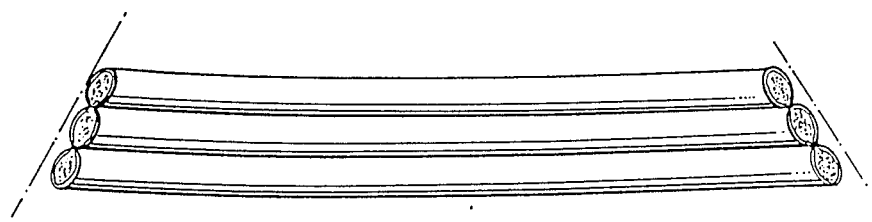
FIG. 4 is a schematic of the manner in which an orthopedic collar according to the invention is cut from a length of orthopedic support material according to the present invention.

Referring first to FIGS. 1 and 2 together, it will be seen that the orthopedic support material of the present invention comprises a core of resilient foam padding (1) which is covered by a fabric material (2). A length of Velcro TM hook and pile closure material (3) is applied to the exterior surface of the covered pad (1,2) along the longitudinal axis thereof. The Velcro TM is sewn to the pad by tough, resilient thread (4) which is applied through the marginal edges of the Velcro TM strip. This manufacturing procedure which is shown best in FIG. 2 results in an orthopedic support structure which is substantially compressed and of higher density along a central longitudinal axis and which is less compressed and softer at its marginal edges. The structure resembles three stacked rolls, divided by the rows of thread (4) which attaches the Velcro TM strip (3) to the pad. It will be noted at this point that while the orthopedic support device of the present invention is being manufactured, a compression and positioning device (5) is used to keep the covering material (2) in place and the foam compressed while the Velcro TM strip (4) is sewn in place.

Ideally, the outer covering material is soft and nonirritating to the skin. Preferably, it is air permeable to disperse body heat and moisture. Moreover, it is preferred that the material chosen resists fraying when cut, as cervical collars manufactured from the support device of the present invention are cut in the field and if the outer covering material frays easily, the cervical collar will tend to come apart.

In one embodiment the outer covering material (2) is a nonwoven material such as one to two ounce weight spun bonded polypropylene. This material is washable, soft, strong, and fray resistant. Preferably, the material is also breathable. Alternatively, other covering materials may include knitted and woven materials. Selection of the covering material depends on the price of available material and availability.

The inner resilient foam pad (1) ought to be an open celled foam which is moisture absorbent and breathable. If used in combination with a non-absorbent outer covering (2) a wicking effect, drawing moisture away from the skin will result.

Ideally, according to the present invention, the padding is made in a range of widths, in gradations of approximately one/half inch. A range of from two inches to five inches is sufficient for the needs of most Fire Departments and emergency medical crews.

Referring next to FIGS. 3 and 4, it will be seen that when a collar as shown in FIG. 3 is custom cut in the field, the ends of the collar are angulated so that they may be brought together at the front of the victim, and closed with a complementary Velcro TM strip (6) (see FIG. 3) to hold the head of the victim in an anatomically correct position. Moreover, because of the angle of the cut as shown in FIG. 4, it will be necessary to provide the device of the present invention in lengths of at least approximately ten to twenty-eight inches, in order to accommodate most victims.

It will be understood that in certain situations, the ends of the collar will be straight cut (i.e. cut at 90° to the side edges of the collar. This will be necessary where, for instance, it is desirable to immobilize the head with the chin up.

Figure 5:
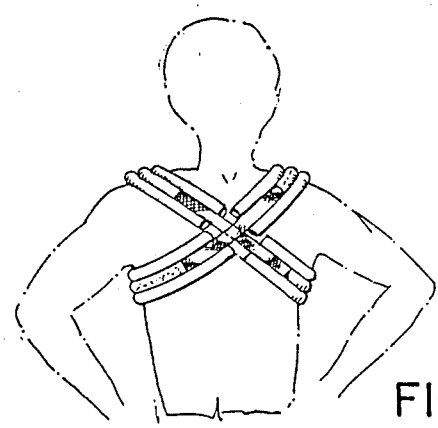
FIG. 5 is a clavicle splint made from orthopedic support material according to the present invention.

The present invention may also be used as a clavicle splint as shown in FIG. 5. A clavicle splint is applied over the shoulders and under the axillae to partially immobilize the shoulders following certain fractures of the clavicle, and dislocation and strains of the sternoclavicular joint. The splint's padding under the axillae acts as a fulcrum to provide lateral traction to the clavicle and the shoulder.

Clavicle splints have previously been proposed and are commercially available. They are illustrated in, for example, U.S. Pat. Nos. 3,338,236, 3,141,465, 3,897,776, and 3,718,137. They are frequently two felt or foam padded, stockinette covered, web shoulder straps joined in the back and incorporating a vertical T-piece in the back. Generally, sized clavicle splints have padded arm sections which are attached to straps for joining to various combinations of retaining devices. These devices are normally available and up to about five sizes in order to ensure that the padded section may be positioned under the axillae and around the shoulders in any patient. The padded sections of these commercially made clavicle straps are of fixed length and may be tapered in shape in order to fit a particular size of patient. In a case where a strap is attached to a padded section, the retaining device (i.e. T-piece) is designed to hold the straps, not the padding. Padded sections of known devices are not adapted to be cut to length, because cutting them to length would effectively eliminate the strap portion thereof.

Other types of known clavicle splints have what is termed a universal size design. However, such splints are none the less available in a variety of sizes, from paediatric to large size adult. These types of splints generally have a cohesive Velcro TM loop fabric laminated only to the top and bottom sides of a strip of foam material. The foam sections generally loop through a fastening ring, back onto themselves where they are joined with a Velcro TM type of material. It will be understood then that the padded sections must be quite thin in order to pass through a ring. The thinness of the padding of this type of design tends to severely limit its usage, and the level of patient comfort available with same. Also, it will be noted that in known 'universal size' clavical splints, the sides of the foram padding are fully exposed, which may result in irritation to the skin.

Referring back to FIG. 5 though it will be seen that the present invention can be used to provide a very simple yet comfortable and economical clavicle splint. Such a splint is made by cutting two sections of the support device of the present invention and providing a closure device capable of joining with the four ends of these two support sections. Such a closure device may be X-shaped, or shaped in any other suitable configuration. Each section of the support material of the present invention is passed over a patient's shoulder to the back where it is fastened to the other device with the use of said X-shaped closure device. It will be seen that such a clavicle splint is very easy to adjust and quite comfortable, as there is no need to limit the thickness of the padding used in it. Moreover, there is no need to manufacture such a clavicle splint in a wide variety of sizes. The same supply of support material may be utilized to make a splint for a very small child and another splint for a very large adult.

Figure 6:
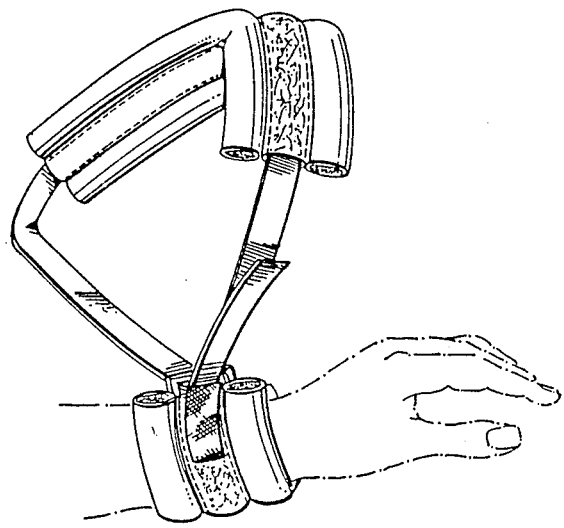
FIG. 6 is a perspective view of a padded arm sling made from orthopedic support material according to the present invention.

Referring lastly to FIG. 6, it will be seen that the present invention may be utilized to provide a novel and comfortable arm sling. A short length of the support material of the present invention is passed around the patient's wrist and fastened together with a Velcro TM strip onto which is threaded a rectangular or a D ring. Through this ring is passed a long strap which is threaded through or likewise attached to a second length of the support material of the present invention, in a lengthwise fashion. This second piece of material may be placed over the victim's shoulder thereby forming a splint.

It is to be understood that the examples described above are not meant to limit the scope of the present invention. It is expected that numerous variants will be obvious to the person skilled in the orthopedic device manufacture and design field, without any departure from the spirit of the present invention. The appended claims, properly construed, form the only limitation upon the slope of the present invention.

I claim:

1. In an orthopedic support device comprising at least one resilient pad having a length, thickness, and width which is covered with a fabric and a pair of ends which are to be fastened together, whereby the support device may be wrapped around a body at a desired location and the ends of said device are fastened together to support the body at that location,
    the improvement wherein said device is provided with a lengthwise-extending first strip of a hook-and-pile closure material, wherein said first strip of closure material is sewn to an exterior surface of said resilient pad along the entire length of said pad, thereby allowing said device to be cut at any selected position along its length so as to provide a support device of any desired shorter length and a second strip of a complementary hook-and-pile closure material for releasably fastening the ends of said device together by attachment to exposed parts of the first strip of closure material on the respective ends of said device.

2. A device as claimed in claim 1, further characterized in that said device is provided in lengths which are greater than or equal to the longest anticipated length required, whereby said device may be cut to a desired length when it is to be used.

3. A device as claimed in claim 1, further comprising a another pad similar to said first-mentioned pad having another pair of ends and similarly provided with a first strip of closure material, so as to form a device having four ends to be fastened together capable of use as a clavicle brace, wherein said second strip of complementary closure material is used to join said four ends of said device together.

4. A device as claimed in claim 3, wherein said second strip is substantially X-shaped.

5. A device as claimed in claim 1, wherein said first strip of closure material is sewn to an intermediate portion of the width of said pad by stitching going entirely through the thickness of said pad so as to substantially divide said pad lengthwise into three parallel lengthwise portions, with one lengthwise portion being directly below said first strip of closure material and the other two lengthwise portions on respective sides thereof.

6. A method of forming an orthopedic support device comprising the steps of:

providing at least one resilient pad having a length, thickness, and width, which is covered with a fabric and has a pair of ends which are to be fastened together;

providing a lengthwise-extending first strip of hook-and-pile closure material, wherein said first strip of closure material is sewn to an exterior surface of said resilient pad over said fabric along the entire length of said pad;

cutting said pad and first strip of closure material sewn thereto at any selected position along its length so as to provide a support device of any desired shorter length; and providing a second strip of a complementary hook-and-pile closure material for releasably fastening the ends of said device together by attachment to exposed parts of the first strip of closure material on the respective ends of said device.

* * * * *